United States Patent [19]

Flamini et al.

[11] Patent Number: 5,274,112

[45] Date of Patent: Dec. 28, 1993

[54] SYNTHESIS OF THE CARBANION 1,1,2-TRICYANO-2-(3,4-DICYANO-5-IMINO-2,5

[75] Inventors: Alberto Flamini, Rignano Flaminio; Nicola Poli, Monterotondo Scalo, both of Italy

[73] Assignee: Consiglio Nazionale Delle Ricerche, Italy

[21] Appl. No.: 909,735

[22] Filed: Jul. 7, 1992

Related U.S. Application Data

[62] Division of Ser. No. 627,576, Dec. 14, 1990, Pat. No. 5,151,527.

[30] Foreign Application Priority Data

Dec. 28, 1989 [IT] Italy .............................. 22867 A/89

[51] Int. Cl.$^5$ ...................... C07F 15/00; C07F 15/02; C07F 15/04; C07F 15/06; C09B 57/04; D06P 1/10
[52] U.S. Cl. ..................... 548/402; 548/453; 8/686
[58] Field of Search ..................... 548/402, 453; 8/686

[56] References Cited

U.S. PATENT DOCUMENTS

| | | | |
|---|---|---|---|
| 2,779,766 | 1/1957 | Middleton | 548/453 |
| 4,111,947 | 9/1978 | L'Eplattenier et al. | 548/402 X |
| 4,666,455 | 5/1987 | Jost et al. | 548/453 X |
| 4,837,326 | 6/1989 | Lin et al. | 548/402 X |
| 4,861,898 | 8/1989 | Radtke et al. | 548/402 |

FOREIGN PATENT DOCUMENTS

63-153545  6/1988  Japan .................................. 548/402

OTHER PUBLICATIONS

Dessy et al., Angew Chem. Int. Ed. Engl., vol. 24(5), pp. 426 to 427 (1985).
Bonamico et al., Angew. Chem. Int. Bd. Engl., vol. 28(8), pp. 1049 to 1050 (1989).
W. Webster et al., "Chemistry of Tetracyanoethylene Anion Radical", Journal of the American Chemical Society, vol. 84, No. 19, Oct. 5, 1962, pp. 3678–3684.
G. Dessy et al., "Synthesis of a Novel Stable Carbanion: 1,1,2-Tricyano-2-(3,4-dicyano-5-imino-2,5-dihydro-1H-pyrrol-2-ylidene)ethanide by Reduction of Tetracyanoethylene with Tris(2,2'-bipyridine)-titanium", Angewandte Chemie, International Edition in English, vol. 24, No. 5, 1985, pp. 426–427.
M. Bonamico et al., "N-Analogues of Metal Acetylacetonates: Bis(1,2,6,7-tetracyano-3,5-diimino-3,5-dihydropyrrolizinido), (metal II=Fe, Ni, Cu, Zn); Crystal Structure of the Copper Derivative", Angewandte Chemie, International Edition in English, vol. 28, No. 8, 1989, pp. 1049–1050.

Primary Examiner—Floyd D. Higel
Attorney, Agent, or Firm—Oliff & Berridge

[57] ABSTRACT

A process is described for preparing the carbanion of the title as its sodium salt with quantitative yields and at a high level of purity, by a two-stage reaction between disodium-tetracyano-ethylene, Lewis acids and water. Metal complexes, prepared from said carbanion, are particularly suited for methods of using the metal complexes as dyes in industrial applications.

2 Claims, No Drawings

SYNTHESIS OF THE CARBANION 1,1,2-TRICYANO-2-(3,4-DICYANO-5-IMINO-2,5

This is a division of application Ser. No. 07/627,576 filed Dec. 14, 1990.

PRIOR ART

The carbanion 1,1,2-tricyano-2-(3,4-dicyano-5-imino-2,5-dihydro-1H-pyrrol-2-ylidene) ethanide, of formula:

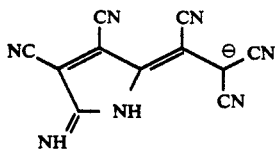

which for simplicity is identified hereinafter as "pyrroliminocyanin", was prepared for the first time as the tetraphenylarsonium salt (As $Ph_4)C_{11}N_7H_2$: see Angew. Chem. Int. Ed. Engl. 24 (1985) 426.

It was subsequently found that this anion when in the presence of a bivalent metal ion isomerizes to give bis-(1,2,6,7-tetracyano-3,5-diimino-3,5-dihydro-pyrrolyzinido) metal, of formula:

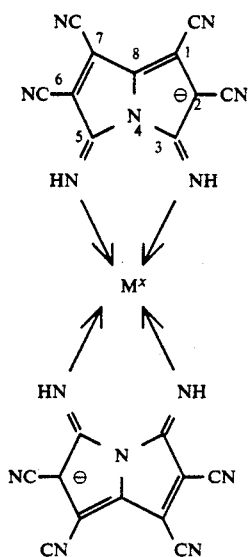

see Angew. Chem. Int. Ed. Engl. 28 (1989) 1049, which describes the crystalline structure of the copper complex of pyrroliminocyanin, $Cu(C_{11}N_7H_2)_2$. The same publication also describes the synthesis of the bivalent zinc, iron and nickel complex analogues. As in the case of the copper complex, these are centre-symmetrical planar metal complexes.

All these complexes are analogues both to the metal acetyl-acetonates, given the method of coordination of the ligand chelating monoanion of $\beta$ type), and to tetracyanoquinodimethane, given the high substitution with cyano groups. For these reasons these complexes are important coordination compounds, useful in the synthesis of molecular materials and in heterogeneous catalysis.

The synthesis of pyrroliminocyanin, described in Angew. Chem. Int. Ed. Engl. 24 (1985) 426, has various drawbacks. Tetracyano-ethylene ($C_6N_4$) is reacted with titanium tris-bipyridyl, which is a pyrophoric substance and therefore difficult to handle. The intermediate complex titanium-bis-bipyridyl-tetracyanoethylene is acidified to separate the desired product int he form of the tetraphenylarsonium salt. The yield is low, about 40%, and column chromatography must be used to obtain a product with an acceptable degree of purity able to give the aforesaid metal complexes.

SUMMARY OF THE INVENTION

A process comprising the condensation of disodium-tetracyano-ethylene in the presence of certain Lewis acids has now been found which enables the sodium slat of pyrroliminocyanin to be obtained with practically quantitative yields. It has also been found that certain metal complexes obtained form pyrroliminocyanin are excellent dyes for industrial applications.

DETAILED DESCRIPTION OF THE INVENTION

The condensation of the disodium-tetracyano-ethylene, which constitutes an aspect of the present invention, takes place in the presence of Lewis acids, of which the following have proved particularly suitable: silicon tetrachloride, chloromethyl-silanes, zinc chloride, aluminum chloride, titanium tri- or tetrachloride, tantalum tetrachloride, niobium pentachloride, chromium dichloride, manganese dichloride, germanium tetrachloride, molybdenum pentachloride, tungsten hexachloride, boron fluoride complexed with ethyl ether, methyltin chlorides.

In order to identify the Lewis acid giving the best yield in promoting the desired condensation, various tests were made on small quantities of reagents, by the following procedure: the disodium-tetracyanoethylene (0.1 g), the solvent (tetrahydro-furan, 10 ml) and the Lewis acid (0.1 g), the solvent (tetrahydro-furan, 10 ml) and the Lewis acid (0.1 g) are enclosed in a glass vial under vacuum. The vial is then heated to 80° C. for three hours under agitation. It is left to cool to ambient temperature, then opened to the air and the contents poured into 50 ml of water. The mixture is filtered and an aqueous solution (10 ml) containing $AsPh_4Cl$(0.2 g) is added to the filtrate. The pyrroliminocyanin tetraphenylarsonium precipitates in variable quantities and purities depending on the Lewis acid.

The preferred Lewis acids are the chloromethylsilanes.

The reaction proceeds in accordance with the following overall scheme:

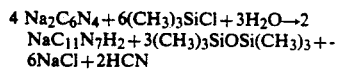

In reality the reaction proceeds in two stages. Int he first stage he disodium-tetracyano-ethylene reacts with the Lewis acid in an organic solvent chosen from ethers (preferably anhydrous tetrahydrofuran), esters (preferably ethyl acetate), aromatics (preferably toluene) and nitriles (preferably acetonitrile). In the second stage water is added.

The disodium-tetracyano-ethylene is prepared, as bis-adduct with dimethoxyethane, by the method described by Webster, Mahler and Benson, J. Am. Chem. Soc. 84 (1962) 3678. The Lewis acids, including trimethylchlorosilane, are commercially assailable products.

The pyrroliminocyanin sodium salt is thus obtained with practically quantitative yields and with sufficient purity for direct use in the synthesis of metal complexes.

It has also been found, and constitutes a further aspect of the present invention, that metal complexes obtainable form the pyrroliminocyanin sodium slat by reaction with metal halides in an aqueous-ether environment, are useful as dyes for plastic materials and fibres.

In this respect, the metalation of the pyrroliminocyanin induces a bathochromic shift of 120 nm and an increase int he absorption coefficient of about 4 times.

The following examples are given as non-limiting illustration of the invention.

EXAMPLE 1

Preparation of Pyrroliminocyanin Sodium Salt 2.94 g of the bis-adduct of $Na_2C_6N_4$ with dimethoxyethane are placed in 90 ml of freshly distilled, deoxygenated anhydrous tetrahydrofuran. 1.81 g of $(CH_3)_3SiCl$ are added to this solution, operating in a nitrogen atmosphere. The solution becomes intensely coloured firstly red and then violet. It is stirred at ambient temperature for 1 hour, then heated under reflux for 3 hours. NaCl precipitates on cooling to ambient temperature. The solvent and excess $(CH_3)_3SiCl$ are eliminated by evaporation under vacuum. The residue is taken up in acetone and the NaCl filtered off. At this point the precaution of operating under nitrogen is no longer necessary. 10 ml of water are added to the violet acetone solution and the water and hexamethyldisiloxane are evaporated under vacuum to obtain a dark green microcrystalline solid of composition $NaC_{11}N_7H_2.2H_2O$ with a quantitative yield and sufficient purity for direct use in the synthesis of meal complexes.

If, after cooling to ambient temperature in the aforesaid procedure, 100 ml of an aqueous solution containing 1.75 g of tetraphenylarsonium chloride $As(C_6H_5)_4Cl$ are added to the violet tetrahydrofuran solution, after evaporation in air until the solution is decolorized, a golden microcrystalline precipitate is obtained, which is filtered off and recrystallized from 1:1 acetone/water by slow evaporation in air. In this manner 2.18 g of $As(C_6H_5)_4C_{11}N_7H_2$ are obtained with I.R and U.V spectroscopic properties identical to those of the product described in Angew. Chem. Int. Ed. Engl. 24 (1985) 426.

EXAMPLE 2

Preparation of the copper complex of pyrroliminocyanin 2 of $NaC_{11}N_7H_2.2H_2O$ prepared in accordance with Example 1 are dissolved in 50 ml of tetrahydrofuran. 100 ml of an aqueous solution containing 7 g of $CuCl_2.2H_2O$ are added to the violet solution. The colour of the solution changes immediately from violet to blue. The aqueous solution is allowed to evaporate in air, and when it has reduced to one half its initial volume 2; 5 g of $Cu(C_{11}N_7H_2)_2.2THF$ precipitate, this having spectroscopic properties identical to those of the product 4c, the structure of which was resolved with X-rays, as described in Angew. Chem. Int. Ed. Engl. 28 (1989) 19050.

The bivalent complexes of nickel and cobalt are prepared in like manner.

Zinc, manganese and iron complexes are also prepared in like manner, however it is necessary to operate in an anhydrous environment (anhydrous tetrahydrofuran under nitrogen), using the respective anhydrous metal dichlorides as stating materials. In this case, it is also necessary to recrystallize the reaction products to separate them from the sodium chloride.

We claim:

1. A method for using metal complexes, of bis-(1,2,6,7-tetracyano-3,5-diimino-3,5-dihydro-pyrrolyzinide) comprising preparing said metal complex by reacting a sodium slat of 1,1,2-tricyano-2-(3,4-dicyano-5-imino-2,5-dihydro-1H-pyrrol-2-ylidene) ethanide with bivalent metal halides and applying said metal complexes as dyes to plastic materials or fibers.

2. A method of dyeing plastic materials or fibers comprising preparing a metal complex having a general formula:

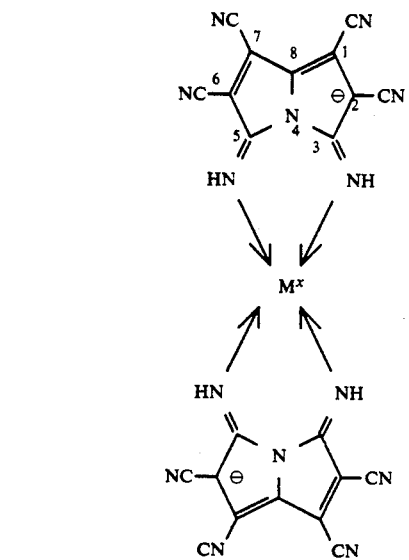

and applying said metal complex to the plastic materials or fibers.